(12) United States Patent
Kim

(10) Patent No.: US 9,075,053 B2
(45) Date of Patent: Jul. 7, 2015

(54) TARGET SUBSTANCE DETECTION METHOD USING APTAMER

(75) Inventor: So Youn Kim, Seoul (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 9 days.

(21) Appl. No.: 13/201,764

(22) PCT Filed: Feb. 16, 2010

(86) PCT No.: PCT/KR2010/000952
§ 371 (c)(1),
(2), (4) Date: Oct. 14, 2011

(87) PCT Pub. No.: WO2010/093223
PCT Pub. Date: Aug. 19, 2010

(65) Prior Publication Data
US 2012/0040865 A1 Feb. 16, 2012

(30) Foreign Application Priority Data

Feb. 16, 2009 (KR) ........................ 10-2009-0012287
Feb. 16, 2009 (KR) ........................ 10-2009-0012288

(51) Int. Cl.
| | | |
|---|---|---|
| C12Q 1/68 | (2006.01) | |
| G01N 33/543 | (2006.01) | |
| C12N 15/11 | (2006.01) | |
| C12N 15/115 | (2010.01) | |

(52) U.S. Cl.
CPC .......... *G01N 33/5438* (2013.01); *C12N 15/111* (2013.01); *C12N 15/115* (2013.01); *C12N 2310/16* (2013.01); *C12N 2320/10* (2013.01); *C12Q 1/6825* (2013.01)

(58) Field of Classification Search
None
See application file for complete search history.

(56) References Cited

U.S. PATENT DOCUMENTS

| | | | | |
|---|---|---|---|---|
| 2002/0037506 | A1* | 3/2002 | Lin et al. ............................. | 435/6 |
| 2003/0064530 | A1* | 4/2003 | Okada et al. ................... | 436/514 |
| 2005/0079520 | A1* | 4/2005 | Wu .................................... | 435/6 |
| 2005/0282226 | A1 | 12/2005 | Okada et al. | |
| 2011/0065086 | A1* | 3/2011 | Bruno ............................... | 435/5 |

OTHER PUBLICATIONS

I. Heller et al., Identifying the Mechanism of Biosensing with Carbon Nanotube Transistors, Nano Letters, 2008, pp. 591-595, vol. 8, No. 2.
Soon H. Kang et al., Nanorod-Based Dye-Sensitized Solar Cells with Improved Charge Collection Efficiency, Advanced Materials, 2008, pp. 54-58, vol. 20.
Yeon S. Kim et al., Electrochemical detection of 17β-estradiol using DNA aptamer immobilized gold electrode chip, Biosensors and Bioelectronics, 2007, pp. 2525-2531, vol. 22.
J. Kong et al., Nanotube Molecular Wires as Chemical Sensors, Science, 2000, pp. 622-625, vol. 287.
Jeong-O Lee et al., Aptamers as molecular recognition elements for electrical nanobiosensors, Anal Bioanal Chem, 2008, pp. 1023-1032, vol. 390.
M. Lee et al., Linker-free directed assembly of high-performance integrated devices based on nanotubes and nanowires, Nature Nanotechnology, 2006, pp. 66-71, vol. 1.
H. Masuda et al., Ordered Metal Nanohole Arrays Made by a Two-Step Replication of Honeycomb Structures of Anodic Alumina, Science, 1995, pp. 1466-1448, vol. 268.
H. Ozaki et al., Biomolecular sensor based on fluorescence-labeled aptamer, Bioorganic & Medicinal Chemistry Letters, 2006, pp. 4381-4384, vol. 16.
Eric S. Snow et al., Capacitance and Conductance of Single-Walled Carbon Nanotubes in the Presence of Chemical Vapors, Nano Letters, 2005, pp. 2414-2417, vol. 5, No. 12.
S. Song et al., Aptamer-based biosensors, Trends in Analytical Chemistry, 2008, pp. 108-117, vol. 27, No. 2.
Charles A. Staples et al., Ultimate Biodegradation of Alkylphenol Ethoxylate Surfactants and Their Biodegradation Intermediates, Environmental Toxicology and Chemistry, 2001, pp. 2450-2455, vol. 20, No. 11.
International Search Report for PCT/KR2010/000952 mailed on Dec. 30, 2010.
Yeon-Seok Kim et al., "Aptamer-Based Biosensor and Separation Technologies", NICE, 2008, pp. 690-695, vol. 26, No. 6.
Shiping Song et al., "Aptamer-based biosensors", Trends in Analytical Chemistry, 2008, pp. 108-117, vol. 27, No. 2.
Kun Liu et al., "Conductance spikes in single-walled carbon nanotube field-effect transistor", Applied Physics Letters, Oct. 18, 1999, pp. 2494-2496, vol. 75, No. 16.

* cited by examiner

*Primary Examiner* — Kimberly Chong
(74) *Attorney, Agent, or Firm* — Rabin & Berdo P.C.

(57) ABSTRACT

The present invention relates to a method and kit of detecting a target material using an aptamer, and more particularly to a method and kit for detecting a target material, in which a sample and a second aptamer are added to a first aptamer immobilized on a solid phase so as to form a bond sandwiched between the first aptamer, the target material and the second aptamer, to an FET sensor-based method and kit for detecting a target material, and to an AAO sensor-based method and kit for detecting a target material.

The inventive method for a target material using an aptamer can detect even low-molecular-weight materials which were difficult to detect in the prior art, thereby enabling detection of disease-related metabolites, environmental pollutants and food toxins in solutions. In addition, the detection method of the present invention is a direct and simple method and is highly cost-effective, because it uses the aptamer which can be consistently reproduced and can be produced at low costs. Thus, the present invention is very useful.

16 Claims, 7 Drawing Sheets

SEQUENCE LISTING

```
<160> NUMBER OF SEQ ID NOS: 30

<210> SEQ ID NO 1
<211> LENGTH: 106
<212> TYPE: DNA
<213> ORGANISM: Artificial
<220> FEATURE:
<223> OTHER INFORMATION: random ssDNA library
<220> FEATURE:
<221> NAME/KEY: misc_feature
<222> LOCATION: (23)..(82)
<223> OTHER INFORMATION: n is a, c, g, or t

<400> SEQUENCE: 1
gggccgttcg aacacgagca tgnnnnnnnn nnnnnnnnnn nnnnnnnnnn nnnnnnnnnn      60
nnnnnnnnnn nnnnnnnnnn nnggacagta ctcaggtcat cctagg                   106

<210> SEQ ID NO 2
<211> LENGTH: 60
<212> TYPE: DNA
<213> ORGANISM: Artificial
<220> FEATURE:
<223> OTHER INFORMATION: bisphenol A aptamer

<400> SEQUENCE: 2
cggccctagg atgacctgag tactgtccct cacccctact tccgccactg gcccaacagc      60

<210> SEQ ID NO 3
<211> LENGTH: 60
<212> TYPE: DNA
<213> ORGANISM: Artificial
<220> FEATURE:
<223> OTHER INFORMATION: bisphenol A aptamer

<400> SEQUENCE: 3
tgcctaggat gacctgagta ctgtccaggc tccgaccttg tccctgccgc cactctccca      60

<210> SEQ ID NO 4
<211> LENGTH: 60
<212> TYPE: DNA
<213> ORGANISM: Artificial
<220> FEATURE:
<223> OTHER INFORMATION: bisphenol A aptamer

<400> SEQUENCE: 4
gcggacgggc tcggctcacc taggatgacc tgagtactgt ccccgtggcg ctaattcggg      60

<210> SEQ ID NO 5
<211> LENGTH: 60
<212> TYPE: DNA
<213> ORGANISM: Artificial
```

```
<220> FEATURE:
<223> OTHER INFORMATION: bisphenol A aptamer

<400> SEQUENCE: 5
cggcccgccc ctaggatgac ctgagtactg tccgcgggac ggtatcgctg agacaggtgc    60

<210> SEQ ID NO 6
<211> LENGTH: 60
<212> TYPE: DNA
<213> ORGANISM: Artificial
<220> FEATURE:
<223> OTHER INFORMATION: bisphenol A aptamer

<400> SEQUENCE: 6
cggcagccct aggatgacct gagtactgtc cgcgaaagac tccatggtac ccggtgctta    60

<210> SEQ ID NO 7
<211> LENGTH: 58
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 7
gggggcgtcg ncctaggatg acctgagtac tgtccgcacn cagggaggat gcattgac      58

<210> SEQ ID NO 8
<211> LENGTH: 60
<212> TYPE: DNA
<213> ORGANISM: Artificial
<220> FEATURE:
<223> OTHER INFORMATION: bisphenol A aptamer

<400> SEQUENCE: 8
gtgtccccac gtcctaggat gacctgagta ctgtccaatg ccgctcctcc cgatgcagac    60

<210> SEQ ID NO 9
<211> LENGTH: 60
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (7)..(7)
<223> OTHER INFORMATION: n is a, c, g, or t

<400> SEQUENCE: 9
ctcttcnctc caattcgtaa gatgacctga ggtctgccca acggtgttta gaacccttg     60

<210> SEQ ID NO 10
<211> LENGTH: 60
<212> TYPE: DNA
<213> ORGANISM: Artificial
<220> FEATURE:
<223> OTHER INFORMATION: bisphenol A aptamer

<400> SEQUENCE: 10
cgcagcgcgc ccctgagtac tgtccgccca acggtgtgac ggccctgcga tcaacgattg    60
```

<210> SEQ ID NO 11
<211> LENGTH: 60
<212> TYPE: DNA
<213> ORGANISM: Artificial
<220> FEATURE:
<223> OTHER INFORMATION: bisphenol A aptamer

<400> SEQUENCE: 11
gggccgtcct aggatgacct gagtactgtc cgcccaacgg tgtgacggcc ctgcgatcaa    60

<210> SEQ ID NO 12
<211> LENGTH: 60
<212> TYPE: DNA
<213> ORGANISM: Artificial
<220> FEATURE:
<223> OTHER INFORMATION: bisphenol A aptamer

<400> SEQUENCE: 12
ccctcgccct gagtactgtc ccccgtccgt ccggtgaggg ccactatcgc taactgatca    60

<210> SEQ ID NO 13
<211> LENGTH: 60
<212> TYPE: DNA
<213> ORGANISM: Artificial
<220> FEATURE:
<223> OTHER INFORMATION: bisphenol A aptamer

<400> SEQUENCE: 13
aggccgttgg tgtggtgggc ctagggccgg cggcgcacag ctgttataga cgtctccagc    60

<210> SEQ ID NO 14
<211> LENGTH: 60
<212> TYPE: DNA
<213> ORGANISM: Artificial
<220> FEATURE:
<223> OTHER INFORMATION: bisphenol A aptamer

<400> SEQUENCE: 14
ccgccgttgg tgtggtgggc ctagggccgg cggcgcacag ctgttataga cgtctccagc    60

<210> SEQ ID NO 15
<211> LENGTH: 60
<212> TYPE: DNA
<213> ORGANISM: Artificial
<220> FEATURE:
<223> OTHER INFORMATION: bisphenol A aptamer

<400> SEQUENCE: 15
ccgccgttgg tgtggtgggc ctagggccgg cggcgcacag ctgttataga cgcctccagc    60

<210> SEQ ID NO 16
<211> LENGTH: 60
<212> TYPE: DNA
<213> ORGANISM: Artificial
<220> FEATURE:
<223> OTHER INFORMATION: bisphenol A aptamer

<400> SEQUENCE: 16
ccgccgttgg tgtggtgggc ccagggccgg cggcgcacag ctgttataga cgcctccagc    60

<210> SEQ ID NO 17
<211> LENGTH: 60
<212> TYPE: DNA
<213> ORGANISM: Artificial
<220> FEATURE:
<223> OTHER INFORMATION: bisphenol A aptamer -continued

<400> SEQUENCE: 17
tgacggtggc gtggagggcg cgtatcaatc gttgatcgca gggccgtcat accgttggag    60

<210> SEQ ID NO 18
<211> LENGTH: 61
<212> TYPE: DNA
<213> ORGANISM: Artificial
<220> FEATURE:
<223> OTHER INFORMATION: bisphenol A aptamer

<400> SEQUENCE: 18
tgacggtggc gtggagggcg cgtatcaatc gttgatcgca gggccgtcat accgttgggg    60
g                                                                    61

<210> SEQ ID NO 19
<211> LENGTH: 60
<212> TYPE: DNA
<213> ORGANISM: Artificial
<220> FEATURE:
<223> OTHER INFORMATION: bisphenol A aptamer

<400> SEQUENCE: 19
tgacggtggc gtggagggcg cgtatcaatc gttgatcgca gggccgtcat accggtcggg    60

<210> SEQ ID NO 20
<211> LENGTH: 60
<212> TYPE: DNA
<213> ORGANISM: Artificial
<220> FEATURE:
<223> OTHER INFORMATION: bisphenol A aptamer

<400> SEQUENCE: 20
gccgacaggg catgggacgc tatcagcggt gtcaatcgaa ttcccgcggc cgccatgcgg    60

<210> SEQ ID NO 21
<211> LENGTH: 60
<212> TYPE: DNA
<213> ORGANISM: Artificial
<220> FEATURE:
<223> OTHER INFORMATION: bisphenol A aptamer

<400> SEQUENCE: 21
ggtccccgca gctcatacgg cgctccagcg taatcgaatt cccgcggccg ccatgcggcc    60

<210> SEQ ID NO 22
<211> LENGTH: 60
<212> TYPE: DNA
<213> ORGANISM: Artificial
<220> FEATURE:
<223> OTHER INFORMATION: bisphenol A aptamer

<400> SEQUENCE: 22
gcgagtggcc catcagcaga gcgtaatccc cacgcacatc gagtgccccc ggccggtgct    60

<210> SEQ ID NO 23
<211> LENGTH: 57
<212> TYPE: DNA
<213> ORGANISM: Artificial
<220> FEATURE:
<223> OTHER INFORMATION: bisphenol A aptamer

<400> SEQUENCE: 23
gtattgtcat tcatatcctc gtgcttgctg tcctcacccc acccaccaga atggaaa       57

```
<210> SEQ ID NO 24
<211> LENGTH: 60
<212> TYPE: DNA
<213> ORGANISM: Artificial
<220> FEATURE:
<223> OTHER INFORMATION: bisphenol A aptamer

<400> SEQUENCE: 24
cctggtattg tcttgccaat cctcgccctg gctgtcttac ccctccccac ccgcctgaag    60

<210> SEQ ID NO 25
<211> LENGTH: 63
<212> TYPE: DNA
<213> ORGANISM: Artificial
<220> FEATURE:
<223> OTHER INFORMATION: bisphenol A aptamer

<400> SEQUENCE: 25
gtcgactcgc gggtaccgtg ctcaatgtcc caatccgggg aagcgtttag acccgcagcc    60
cac                                                                 63

<210> SEQ ID NO 26
<211> LENGTH: 58
<212> TYPE: DNA
<213> ORGANISM: Artificial
<220> FEATURE:
<223> OTHER INFORMATION: bisphenol A aptamer
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 26
gtcgccactg cgggtaccgt gcttgggcna ccgatgnacc ntgnnaccgt gtttngcc      58

<210> SEQ ID NO 27
<211> LENGTH: 63
<212> TYPE: DNA
<213> ORGANISM: Artificial
<220> FEATURE:
<223> OTHER INFORMATION: bisphenol A aptamer

<400> SEQUENCE: 27
ccggtgggtg gtcaggtggg atagcgttcc gcgtatggcc cagcgcatca cgggttcgca    60
cca                                                                 63

<210> SEQ ID NO 28
<211> LENGTH: 60
<212> TYPE: DNA
<213> ORGANISM: Artificial
<220> FEATURE:
<223> OTHER INFORMATION: bisphenol A aptamer
```

```
<400> SEQUENCE: 28
gggcggtggg tggcgagttg tgagacgctg gaggaggttg ctgccccgg cacattggga    60

<210> SEQ ID NO 29
<211> LENGTH: 22
<212> TYPE: DNA
<213> ORGANISM: Artificial
<220> FEATURE:
<223> OTHER INFORMATION: fragment attached to 2nd aptamer

<400> SEQUENCE: 29
gggccgttcg aacacgagca tg                                           22

<210> SEQ ID NO 30
<211> LENGTH: 22
<212> TYPE: DNA
<213> ORGANISM: Artificial
<220> FEATURE:
<223> OTHER INFORMATION: Cy3-attached fragment

<400> SEQUENCE: 30
catgctcgtg ttcgaacggc cc                                           22
```

TARGET SUBSTANCE DETECTION METHOD USING APTAMER

TECHNICAL FIELD

The present invention relates to a method and kit of detecting a target material using an aptamer, and more particularly to a method and kit for detecting a target material, in which a sample and a second aptamer are added to a first aptamer immobilized on a solid phase so as to form a bond sandwiched between the first aptamer, the target material and the second aptamer, to an FET sensor-based method and kit for detecting a target material, and to an AAO sensor-based method and kit for detecting a target material.

BACKGROUND ART

Development of novel sensor platforms for sensitively and specifically detecting small molecules in solutions is very important for monitoring of disease-related metabolites, environmental pollutants and food toxins. Low-molecular-weight materials, such as metabolites, environmental pollutants and food toxins, have generally been analyzed by complex techniques, such as GC/MS or HPLC, which are time-consuming even by skilled workers and cannot be applied to on-site analysis (Stales, C. A. et al, *Environ. Toxicol. Chem.*, 20: 2450, 2001). In order to succeed in on-site real-time detection, small-scale systems and specific binding reagents have been required.

As portable platforms for detecting small-molecular-weight materials, detection platforms such as surface plasmon resonance platforms are known, but it is known that it is difficult for these platforms to detect materials having a very low molecular weight of 400 or less. In addition, it was reported that, when analysis was conducted using an aptamer specifically binding to 17-β-estradiol (MW: 272) at the concentration of 1 µM (272 ppb), analysis for low-molecular-weight materials as described above is impracticable as shown in FIG. 1 (Kim et al., *Biosens. Bioelectron.*, 22:2525, 2007). Thus, development of novel platforms capable of detecting even low-molecular-weight materials in a specific and sensitive manner has been demanded.

Also, for specific and sensitive detection of analytes, reagents specifically binding to analytes such as antibodies are required. However, low-molecular-weight materials are generally too small to generate antibodies in animals or are strongly toxic such that they cannot produce antibodies. For this reason, novel specific binding reagents targeting small molecules have been demanded.

Meanwhile, the term "aptamer" as used herein refers to a single-stranded oligonucleotide (single-stranded DNA or RNA molecule) that can bind specifically to its target with high affinity. The aptamer can be used as a biosensor element capable of binding to a molecule in a detection/analysis system, and thus has been recognized as a substitutive for antibody. Particularly, the aptamers can be used as molecules targeting various organic and inorganic materials, including toxins, unlike antibodies, and once an aptamer binding specifically to a certain material is isolated, it can be consistently reproduced at low costs using automated oligomer synthesis methods. Since an aptamer-based biosensor of measuring a target protein using a fluorescence-labeled aptamer was first developed in 1996, various aptamer biosensors have been developed based on the advantages and structural properties of the aptamer (Yeon-Seok KIM & Man-Bock GU, NICE, 26(6):690, 2008).

However, prior analysis methods employing aptamers were competitive analysis methods in an aptamer attached to a specific material is detached or allowed to bind to other materials. Thus, development of a method of using an aptamer to detect a material in a more direct and simple manner has been required.

Meanwhile, carbon nanotube (CNT)-based biosensors are highly attractive portable platforms for detecting small-molecular-weight materials. Single-wall carbon nanotube (swCNT)-field effect transistors (FETs) were useful as small-scale sensors for highly sensitively detecting chemical materials, compared to other detection platforms, such as quartz-crystal microbalance sensors, electrochemical impedance spectrometry sensors, surface plasmon resonance sensors and light-addressable potentiometric sensors (LAPSs) (Kim, T. K. et al., *Advanced Materials*, 20:1, 2008; Kong, J. et al., *Science*, 287:622, 2000; Snow, E. S. & Perkins, F. K., *Nano. Lett.*, 5:2414, 2005).

However, recent swCNT-FET for detecting small molecules have been limited only to a gas or vapor phase rather than a liquid phase containing most biological metabolites or toxins of interest. In addition, because detection of non-polar small molecules in solutions was not within the detection range of FET-based sensors, it was difficult to detect small molecules using the FET-based sensors (Heller, I. et al, *Nano. Lett.*, 8:591, 2008).

For specific and sensitive detection of analytes, swCNT-FET sensors are required to have specific binding reagents such as antibodies as functional groups, and small molecules are generally too small to generate antibodies in animals or are strongly toxic such that they cannot produce antibodies.

Thus, the present inventors have made extensive efforts to provide a novel detection method capable of detecting even a small molecule, particularly in a solution, and, as a result, have found that, when a sample and a second aptamer are added to a first aptamer immobilized on a solid phase so as to form a bond sandwiched between the first aptamer, the target material and the second aptamer, even a non-polar low-molecular-weight material such as bisphenol A can then be detected, thereby completing the present invention.

The present inventors have also found that even a non-polar low-molecular-weight material present at the pM level can be detected by immobilizing a first aptamer as a probe on an FET sensor, adding a sample and a second aptamer thereto, and then measuring a change in electric current in the FET sensor, thereby completing the present invention.

The present inventors have also found that even a non-polar low-molecular-weight material can be detected by immobilizing an aptamer as a probe on an AAO sensor, adding a sample thereto, and then measuring a change in capacitance in the AAO sensor, thereby completing the present invention.

DISCLOSURE OF INVENTION

Technical Problem

It is an object of the present invention to provide a novel method for detecting a target material, which can detect even a low-molecular-weight material in a solution.

Another object of the present invention is to provide a kit for detecting a target material, which can detect even a low-molecular-weight material in a solution.

Technical Solution

To achieve the above objects, the present invention provides a method of detecting a target material using aptamers, the method comprising the steps of:

(a) adding a sample containing a target material, and a second aptamer binding specifically to the target material and having a label attached thereto, to a first aptamer immobilized on a solid phase and binding specifically to the target material, to form a mixture, and incubating the mixture; and (b) analyzing the label to detect the target material.

The present invention also provides a method of detecting a target material using aptamers, the method comprising the steps of:

(a) adding a sample containing a target material, and a second aptamer binding specifically to the target material, to a first aptamer immobilized on a solid phase and binding specifically to the target material, to form a mixture, and incubating the mixture;

(b) binding a label to the second aptamer; and (c) analyzing the label to detect the target material.

The present invention also provides a kit for detecting a target material, the kit comprising: a solid phase having immobilized thereon a first aptamer binding specifically to the target material; and a detection reagent containing a second aptamer binding specifically to the target material.

The present invention also provides a kit for detecting bisphenol A, the kit comprising: a solid phase having immobilized thereon a first aptamer binding specifically to bisphenol A; and a detection reagent containing a second aptamer which has a label attached thereto and binds specifically to bisphenol A, wherein the first aptamer or the second aptamer is selected from among aptamers represented by nucleic acid sequences of SEQ ID NOS: 2 to 28.

The present invention also provides a nucleic acid fragment for labeling an aptamer, the nucleic acid fragment having a label attached thereto and being capable of complementarily binding to the end of the aptamer.

The present invention also provides a field effect transistor (FET) sensor-based method of detecting a target material using aptamers, the method comprising the steps of:

(a) adding a sample containing a target material, and a second aptamer binding specifically to the target material, to an FET sensor comprising a substrate, a source metal electrode and a drain metal electrode, which are formed on both sides of the substrate, respectively, and a gate formed on the substrate so as to come into contact with the source and drain metal electrodes, wherein the first aptamer binding specifically to the target material is immobilized as a probe on any one or more of the surfaces of the source metal electrode, the gate and the drain metal electrode; and (b) measuring a change in electric current between the source metal electrode and drain metal electrode of the FET sensor, the change occurring when the target material and the second aptamer bind to the first aptamer immobilized on the FET sensor, thereby detecting the target material.

The present invention also provides a kit for detecting a target material, the kit comprising:

an FET sensor comprising a substrate, a source metal electrode and a drain metal electrode, which are formed on both sides of the substrate, respectively, and a gate formed on the substrate so as to come into contact with the source and drain metal electrodes, wherein the first aptamer binding specifically to the target material is immobilized as a probe on any one or more of the surfaces of the source metal electrode, the gate and the drain metal electrode; and a detection reagent containing a second aptamer binding specifically to the target material.

The present invention also provides a kit for detecting bisphenol A, the kit comprising: an FET sensor comprising a substrate, Au electrodes formed on both sides of the substrate, respectively, and a channel region comprising single-wall carbon nanotubes which come into contact with the Au electrodes and are provided on the substrate to form a channel, wherein a first aptamer binding specifically to bisphenol A is immobilized as a probe on the surface of the Au electrodes; and a detection reagent containing a second aptamer binding specifically to bisphenol A, wherein the first aptamer or the second aptamer is selected from among aptamers represented by nucleic acid sequences of SEQ ID NOS: 2 to 28.

The present invention also provides an anodic aluminum oxide (AAO) sensor-based method of detecting a target material using aptamers, the method comprising the steps of:

(a) adding a sample containing a target material to an AAO sensor comprising a substrate, an anodic aluminum oxide formed on the substrate and having nano-sized pores, and a metal coated on the surface of the anodic aluminum oxide, wherein an aptamer binding specifically to the target material is immobilized as a probe on the surface of the metal; and (b) measuring a change in the capacitance of the AAO sensor, the change occurring when the target material binds to the aptamer, thereby detecting the target material.

The present invention also provides a kit for detecting a target material, the kit comprising: an anodic aluminum oxide (AAO) sensor comprising a substrate, an anodic aluminum oxide formed on the substrate and having nano-sized pores, and a metal coated on the surface of the anodic aluminum oxide; and an aptamer binding specifically to the target material.

Other features and embodiments of the present invention will be more apparent from the following detailed descriptions and the appended claims.

BRIEF DESCRIPTION OF THE DRAWINGS

FIG. 8 shows the results of detecting bisphenol using an AAO sensor, wherein FIG. 8(a) shows the results of an experiment carried out using an AAO sensor to which no aptamer was bound, and FIG. 8(b) shows the results of measuring changes in capacitance in an AAO sensor to which an aptamer was bound.

BEST MODE FOR CARRYING OUT THE INVENTION

Figure 1:
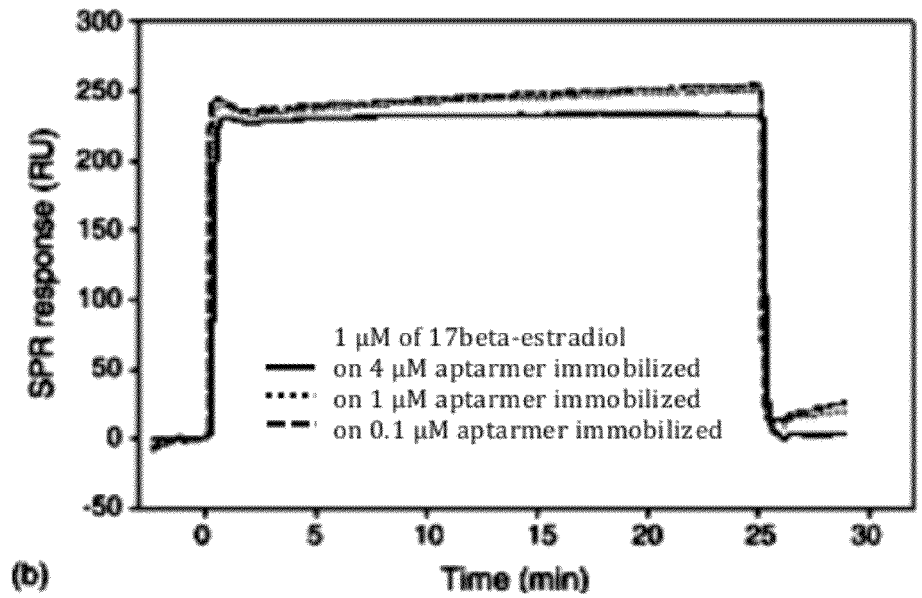
FIG. 1 shows the results of carrying out the detection of 17-β-estradiol using an aptamer according to the prior art SPR method.
Figure 2:
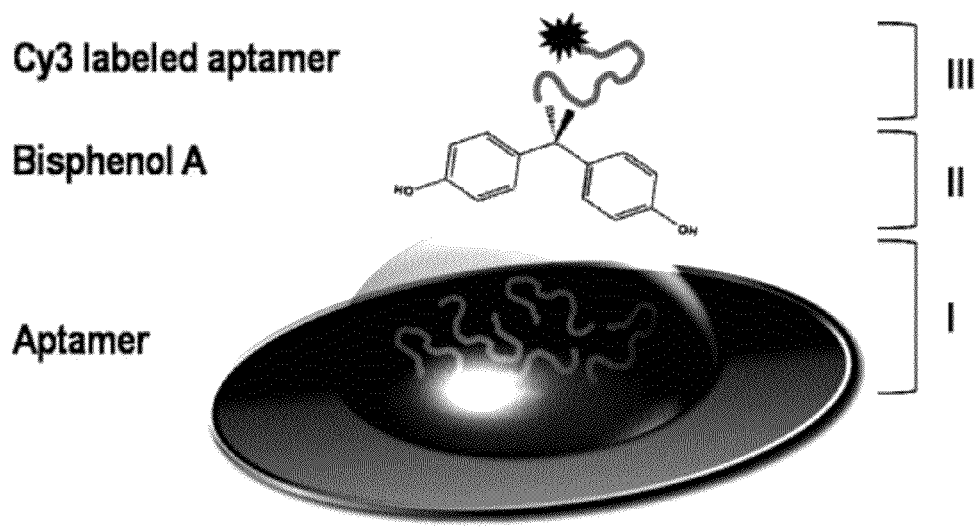
FIG. 2 is a schematic view showing a process of binding a bisphenol A and a labeled aptamer to an immobilized aptamer according to a method of the present invention.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows.

As used herein, the term "aptamer" refers to a single-stranded oligonucleotide that can bind to its target with high affinity.

As used herein, the term "sample" refers to a composition that might contain a target material of interest to be analyzed. It may be detected in a sample collected from one or more of liquids, soil, air, food, waste, animal and plant organs, and animal and plant tissues, but is not limited thereto. Herein, the liquids may be water, blood, urine, tears, sweat, salvia, lymph and cerebrospinal fluids, the water includes river water, seawater, lake water and rainwater, the waste includes sewage and wastewater, and the animals include the human body. Also, the animal and plant tissues include the tissues of mucosas, skins, shells, hairs, scales, eyeballs, tongues, cheeks, hoofs, beaks, mouths, feet, hands, lips, nipples, ears, noses and the like.

As used herein, the term "field effect transistor (FET) sensor" means a sensor comprising a substrate, source and drain metal electrodes formed on both sides of the substrate so as to have a polarity opposite to that of the substrate, and a gate formed on the substrate while coming into contact with the source and drain metal electrodes, wherein a probe is immobilized on the surface of the gate or the surface of the metal electrodes, such that binding between the probe and the target material is detected by electrically measuring a change in electric current, which occurs when the target material binds to the probe.

As used herein, the term "carbon nanotubes" refers to a material in which one carbon atom bonds to other carbon atoms to form a hexagonal honeycomb and which has a diameter on the nanometer scale. Carbon nanotubes can be classified, according to the number of graphite sheets rolled, into single-walled nanotubes, multi-walled nanotubes, and rope nanotubes.

As used herein, the term "anodic aluminum oxide" (AAO) refers to a nono-sized porous alumina having regularity on the surface, formed using an anodization process of electro-chemically oxidizing aluminum.

In one aspect, the present invention is directed to a method of detecting a target material using aptamers, the method comprising the steps of:

(a) adding a sample containing a target material, and a second aptamer binding specifically to the target material and having a label attached thereto, to a first aptamer immobilized on a solid phase and binding specifically to the target material, to form a mixture, and incubating the mixture; and (b) analyzing the label to detect the target material.

As used herein, the term "solid phase" refers to a solid-state support on which an aptamer is immobilized. The shape or material of the solid phase is not limited, as long as an aptamer is immobilized thereon. To perform analysis in a convenient manner, a multi-well microplate may generally be used. In addition, other shapes, such as sensor chips, and columns packed with plastic, polypropylene, sepharose or agarose beads, may also be used.

The first aptamer may be immobilized on the solid phase using a conventional method. In one Example of the present invention, the first aptamer was immobilized by a sol-gel method, it will be obvious to a person skilled in the art that the method of immobilizing the first aptamer is not limited to the sol-gel method.

In the present invention, step (a) is a step of adding the sample and the second aptamer to the first aptamer immobilized on the solid phase and incubating the mixture, and the term "incubating" as used herein means adding the sample and the second aptamer to the first aptamer and incubating the first aptamer such that the target material present in the sample binds to the immobilized first aptamer and the second aptamer binds to the target material. The step (a) may be performed by mixing the sample with the second aptamer, and then adding the mixture to the first aptamer. Specifically, the step (a) may be performed by mixing the sample with the second aptamer to form a specific bond between the target material and the second aptamer, and then adding the mixture to the first aptamer to form a bond between the first aptamer, the target material and the second aptamer.

Also, the step (a) may be performed by adding the sample to the first aptamer, and then adding the second aptamer thereto. Specifically, the step (a) may be performed by adding the sample to the first aptamer immobilized on the solid phase to form a bond between the target material in the sample and the first aptamer, and then adding the second aptamer thereto to form a bond between the first aptamer, the target material and the second aptamer.

The label which is attached to the second aptamer may be attached using a direct or indirect method, and examples of the label include, but not limited to, fluorescent materials, radioisotopes and the like. Herein, examples of the fluorescent materials include, but not limited to, fluorescent dyes such as Cy3 or Cy5, and fluorescent proteins such as luciferase or GFP.

In the present invention, the step (b) is a step of analyzing the label to detect the target material. In this step, a change in the label, which occurs when the target material and the second aptamer bind to the first aptamer immobilized on the solid phase, is analyzed to detect the target material. Herein, analysis of the label may be performed using generally known methods for analyzing label target materials. For example, if a fluorescent material is used as the label, luminescence or a change in color will occur, and thus the target material may be detected by measuring the generated luminescence or color change. For example, whether the target material was detected may be determined by scanning a well, in which a reaction occurred, by an image scanner capable of detecting a fluorescent dye. Also, the amount of target material detected can be determined by measuring the intensity of the image using software.

In addition to detecting the target material using the label attached to the second aptamer, the target material may be detected by binding the sample and the second aptamer to the first aptamer in the step (a), and then binding the label to the second aptamer.

In another aspect, the present invention is also directed to method of detecting a target material using aptamers, the method comprising the steps of:

(a) adding a sample containing a target material, and a second aptamer binding specifically to the target material, to a first aptamer immobilized on a solid phase and binding specifically to the target material, to form a mixture, and incubating the mixture;

(b) binding a label to the second aptamer; and (c) analyzing the label to detect the target material.

In the present invention, binding the label in step (b) may be performed by complementarily binding a nucleic acid fragment to the second aptamer.

As used herein, the term "complementarily binding" means that about 80-90% or more, preferably about 90-95% or more, and more preferably 95-99% or more of the sequence of the synthesized nucleic acid fragment is complementary to the second aptamer, or that the sequence of the nucleic acid fragment may be completely complementary to the second aptamer.

Preferably, the nucleic acid fragment may complementary bind to the end of the second aptamer, in which the second aptamer may comprise an additional sequence at its end to perform the complementary binding.

In one Example of the present invention, in order to examine whether the detection method of the present invention can detect a low-molecular-weight material in a solution, an experiment was carried out to determine whether the detection method of the present invention detects bisphenol A, an environmental hormone which has been known to very difficult to detect. As a result, it was found that even low-molecular-weight bisphenol A was specifically detected by the detection method of the present invention. This suggests that the use of the method according to the present invention allows detection of metabolites, toxins and the like in solutions, unlike prior art methods in which the detection of metabolites, toxins and the like in solutions is very difficult.

In the present invention, the aptamer which is used to detect bisphenol A may preferably be selected from aptamers represented by nucleic acid sequences of SEQ ID NOS: 2 to 28. The nucleic acid aptamer is provided as a single-stranded DNA or RNA. Thus, it will be obvious to a person skilled in the art that, if the nucleic acid is RNA, T in the nucleic acid sequence is expressed as U, and that this sequence falls within the scope of the present invention.

In still another aspect, the present invention is also directed to a field effect transistor (FET) sensor-based method of detecting a target material using aptamers, the method comprising the steps of:

(a) adding a sample containing a target material, and a second aptamer binding specifically to the target material, to an FET sensor comprising a substrate, a source metal electrode and a drain metal electrode, which are formed on both sides of the substrate, respectively, and a gate formed on the substrate so as to come into contact with the source and drain metal electrodes, wherein the first aptamer binding specifically to the target material is immobilized as a probe on any one or more of the surfaces of the source metal electrode, the gate and the drain metal electrode; and (b) measuring a change in electric current between the source metal electrode and drain metal electrode of the FET sensor, the change occurring when the target material and the second aptamer bind to the first aptamer immobilized on the FET sensor, thereby detecting the target material.

The method according to the present invention is based on the field effect transistor (FET) principle and is characterized by using the aptamer as a probe immobilized on any one or more of the source metal electrode surface, the gate surface and the drain metal electrode surface. The FET sensor that is used in the present invention may be any FET sensor known in the art. Also, the FET sensor comprises a substrate, source and drain electrodes formed on both sides of the substrate so as to have a polarity opposite to that of the substrate, and a gate formed on the substrate while coming into contact with the source and drain electrodes, and electrically measures a change in electric current, which occurs when the target material binds to the probe immobilized on the gate surface or the source and drain metal electrodes. It will be obvious to a person skilled in the art that any sensor employing this principle may be used to perform the method of the present invention. In addition, in the present invention, the metal electrodes may be formed of any one or more selected from the group consisting of gold, platinum, chromium, copper, aluminum, nickel, palladium and titanium.

For increased detection activity, the FET sensor is preferably an FET sensor in which carbon nanotubes are deposited on the substrate so as to come into contact with the source and drain metal electrodes, thereby forming a channel between the source and drain metal electrodes. Herein, deposition of carbon nanotubes can be performed by conventional processes, including chemical vapor deposition, laser ablation, electric discharge, plasma-enhanced chemical vapor deposition, thermal chemical vapor deposition, vapor phase synthesis, electrolysis, and flame synthesis processes. In this carbon nanotube FET sensor, the first aptamer is preferably immobilized on metal electrode surface.

In the present invention, step (a) is a step of adding the sample and the second aptamer to the FET sensor and may be performed by mixing the sample with the second aptamer and then adding the mixture to the FET sensor. Specifically, the step (a) may be performed by mixing the sample with the second aptamer to foam a specific bond between the target material in the sample and the second aptamer, and then adding the mixture to the FET sensor to form a bond between the first aptamer (serving as a probe), the target material and the second aptamer.

Alternatively, the step (a) may be performed by adding the sample to the FET sensor, and then adding the second aptamer to the FET sensor. Specifically, the step (a) may be performed by adding the sample to the FET sensor such that the target material in the sample binds to the first aptamer of the FET sensor, and then adding the second aptamer to the FET sensor to form a bond between the first aptamer, the target material and the second aptamer.

As used herein, the term "sample" refers to a composition that might contain a target material of interest to be analyzed. It may be detected in a sample collected from one or more of liquids, soil, air, food, waste, animals, plants, animal and plant organs, and animal and plant tissues, but is not limited thereto. Herein, the liquids may be water, blood, urine, tears, sweat, salvia, lymph and cerebrospinal fluids, the water includes river water, seawater, lake water and rainwater, the waste includes sewage and wastewater, and the animals include the human body. Also, the animal and plant tissues include the tissues of mucosas, skins, shells, hairs, scales, eyeballs, tongues, cheeks, hoofs, beaks, mouths, feet, hands, lips, nipples, ears, noses and the like.

In one Example of the present invention, in order to examine whether the detection method of the present invention can detect a non-polar, low-molecular-weight material in a solution, an experiment was carried out to determine whether the detection method of the present invention detects bisphenol A, an environmental hormone which has been known to very difficult to detect. As a result, it was found that, according to the method of the present invention, bisphenol A in solution could be detected even at the pM level, and only bisphenol A was specifically detected without causing a reaction with other bisphenol groups, such as BPB and 6F, which has structures very similar to that of bisphenol A. This suggests that the use of the method according to the present invention allows detection of metabolites, toxins and the like in solutions, unlike prior art methods in which the detection of metabolites, toxins and the like in solutions is very difficult.

In the present invention, the aptamer which is used in the FET sensor to detect bisphenol A may preferably be selected from aptamers represented by nucleic acid sequences of SEQ ID NOS: 2 to 28. The nucleic acid aptamer is provided as a single-stranded DNA or RNA. Thus, it will be obvious to a person skilled in the art that, if the nucleic acid is RNA, T in the nucleic acid sequence is expressed as U, and that this sequence falls within the scope of the present invention.

In yet another aspect, the present invention is also directed to an anodic aluminum oxide (AAO) sensor-based method of detecting a target material using aptamers, the method comprising the steps of:

(a) adding a sample containing a target material to an AAO sensor comprising a substrate, an anodic aluminum oxide formed on the substrate and having nano-sized pores, and a metal coated on the surface of the anodic aluminum oxide, wherein an aptamer binding specifically to the target material is immobilized as a probe on the surface of the metal; and (b) measuring a change in the capacitance of the AAO sensor, the change occurring when the target material binds to the aptamer, thereby detecting the target material.

As used herein, the term "anodic aluminum oxide" (AAO) refers to an aluminum oxide formed using an electrical method. Aluminum has fine nanopores which are regularly aligned in a vertical direction, in which the size of the nonopores can be controlled through an electrical oxidation process. When the surface of this anodic aluminum oxide is coated with metal particles, after which the aptamer is bound to the metal particles, a nanobiosensor can be obtained. When a target material such as bisphenol A reacts selectively with the aptamer in the biosensor, changes in voltage and current will occur, resulting in a change in capacitance, suggesting that even tract materials can be detected by the biosensor. The AAO sensor which is used in the present invention may be any AAO sensor known in the art.

Herein, the metal which is coated on the surface of the anodic aluminum oxide is preferably gold, but is not limited thereto.

Meanwhile, immobilization of the aptamer on the AAO sensor can be performed using a functional group bound to one end of the aptamer. In one Example of the present invention, the thiol group bound to the 3' end of the aptamer was covalently bonded to the gold of the surface of the anodic aluminum oxide, whereby the aptamer was bounded to the surface of the AAO sensor.

Figure 6:
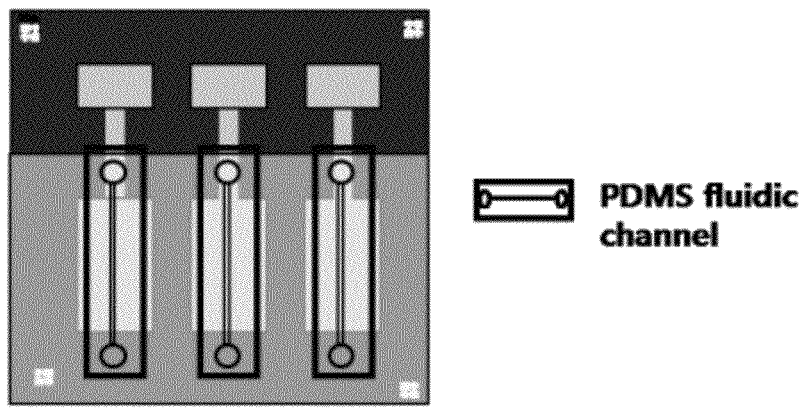
FIG. 6 is a schematic view of a multi-channel AAO sensor.

Preferably, the AAO sensor may have a multi-channel structure as shown in FIG. 6, such that it can detect various materials at the same time. Specifically, different aptamers may be immobilized on different channels such that various materials can be detected at the same time. Alternatively, different samples are introduced into different channels such that various samples can be analyzed at the same time.

In one Example of the present invention, in order to examine whether the AAO sensor-based detection method of the present invention can detect even a non-polar, low-molecular-weight material in a solution, an experiment was carried out to determine whether the detection method of the present invention detects bisphenol A, an environmental hormone which has been known to very difficult to detect. As a result, it was found that bisphenol A in a solution was detected according to the method of the present invention. This suggests that the use of the method according to the present invention allows detection of metabolites, toxins and the like in solutions, unlike prior art methods in which the detection of metabolites, toxins and the like in solutions is very difficult.

In the present invention, the aptamer which is used in the AAO sensor to detect bisphenol A may preferably be selected from aptamers represented by nucleic acid sequences of SEQ ID NOS: 2 to 28. The nucleic acid aptamer is provided as a single-stranded DNA or RNA. Thus, it will be obvious to a person skilled in the art that, if the nucleic acid is RNA, T in the nucleic acid sequence is expressed as U, and that this sequence falls within the scope of the present invention.

Meanwhile, the method of the present invention may be provided in the form of kit in order to increase portability. Specifically, in another aspect, the present invention relates to a kit for detecting a target material, the kit comprising: a solid phase having immobilized thereon a first aptamer binding specifically to the target material; and a detection reagent containing a second aptamer binding specifically to the target material. Herein, the detection reagent containing the second aptamer may be provided in a separate container or in a reaction unit for forming a bond between the target material and the aptamers. In addition, the detection kit may further comprise a detection buffer. Preferably, the detection kit may further comprise an instrument for mixing the detection reagent with the sample.

In a further aspect, the present invention also provides a kit for detecting a target material, the kit comprising:

an FET sensor comprising a substrate, a source metal electrode and a drain metal electrode, which are formed on both sides of the substrate, respectively, and a gate formed on the substrate so as to come into contact with the source and drain metal electrodes, wherein the first aptamer binding specifically to the target material is immobilized as a probe on any one or more of the surfaces of the source metal electrode, the gate and the drain metal electrode; and a detection reagent containing a second aptamer binding specifically to the target material.

Herein, the detection reagent containing the second aptamer may be provided in a separate container or in a reaction unit for forming a bond between the target material and the aptamers. In addition, the detection kit may further comprise a detection buffer. Preferably, the detection kit may further comprise an instrument for mixing the detection reagent with the sample.

In a still further aspect, the present invention also provides a kit for detecting a target material, the kit comprising: an anodic aluminum oxide (AAO) sensor comprising a substrate, an anodic aluminum oxide formed on the substrate and having nano-sized pores, and a metal coated on the surface of the anodic aluminum oxide; and an aptamer binding specifically to the target material.

Preferably, the metal may be gold, but is not limited thereto. The aptamer may be immobilized to AAO sensor using a functional group bound to the end of the aptamer, wherein the functional group may be a thiol group and may be bound by adsorption or bound by a linker. In addition, the kit may further comprise a flow system. As used herein, the term "flow system" means a system allowing a binding buffer containing the sample or the aptamer to flow into the AAO sensor.

The kit for detecting the target material may take the form of bottles, tubs, sachets, envelops, tubes, ampoules, and the like, which may be formed in part or in whole from plastic, glass, paper, foil, wax, and the like. The containers may be equipped with a fully or partially detachable lid that may initially be part of the container or may be affixed to the container by mechanical, adhesive, or other means. The container may also be equipped with a stopper, allowing access to the contents by a syringe needle. The kit may comprise an exterior package which may include instructions regarding the use of the components.

EXAMPLES

Hereinafter, the present invention will be described in further detail with reference to examples. It will be obvious to those skilled in the art that these examples are illustrative purposes only and are not to be construed to limit the scope of the present invention.

In particular, in Examples below, the detection of bisphenol was performed using an aptamer binding specifically to bisphenol A. However, it will be obvious to a person skilled in the art that the method of the present invention can also be applied to detect target materials other than bisphenol A using aptamers binding specifically to the other target materials.

Example 1

Isolation of an Aptamer Binding Specifically to Bisphenol A and Preparation of a Sol-gel Chip Having the Aptamer Immobilized Thereon 1-1: Isolation of Aptamer Binding Specifically to Bisphenol A First, a random ssDNA library having the following sequences was synthesized chemically and isolated by PAGE (Genotech Inc., Korea).

```
                                              (SEQ ID NO: 1)
5'-GGGCCGTTCGAACACGAGCATG-N60-GGACAGTACTCAGGTCATC
CTAGG-3'
```

For the ssDNA pool, the SELEX selection and amplification process was carried out 12 times using a bisphenol A-agarose affinity column, thereby selecting a total of 27 of the following bisphenol A-specific aptamers.

```
#31
                                              (SEQ ID NO: 2)
5'-CGGCCCTAGG ATGACCTGAG TACTGTCCCT CACCCCTACT

TCCGCCACTG GCCCAACAGC-3'

#23
                                              (SEQ ID NO: 3)
5'-TGCCTAGGAT GACCTGAGTA CTGTCCAGGC TCCGACCTTG

TCCCTGCCGC CACTCTCCCA-3'

#47
                                              (SEQ ID NO: 4)
5'-GCGGACGGGC TCGGCTCACC TAGGATGACC TGAGTACTGT

CCCCGTGGCG CTAATTCGGG-3'

#50
                                              (SEQ ID NO: 5)
5'-CGGCCCGCCC CTAGGATGAC CTGAGTACTG TCCGCGGGAC

GGTATCGCTG AGACAGGTGC-3'

#41
                                              (SEQ ID NO: 6)
5'-CGGCAGCCCT AGGATGACCT GAGTACTGTC CGCGAAAGAC

TCCATGGTAC CCGGTGCTTA-3'

#27
                                              (SEQ ID NO: 7)
5'-GGGGGCGTCG NCCTAGGATG ACCTGAGTAC TGTCCGCACN

CAGGGAGGAT GCATTGAC-3'

#45
                                              (SEQ ID NO: 8)
5'-GTGTCCCCAC GTCCTAGGAT GACCTGAGTA CTGTCCAATG

CCGCTCCTCC CGATGCAGAC-3'

#11
                                              (SEQ ID NO: 9)
5'-CTCTTCNCTC CAATTCGTAA GATGACCTGA GGTCTGCCCA

ACGGTGTTTA GAACCCCTTG-3'

#12-3
                                             (SEQ ID NO: 10)
5'-CGCAGCGCGC CCCTGAGTAC TGTCCGCCCA ACGGTGTGAC

GGCCCTGCGA TCAACGATTG-3'

#12-4
                                             (SEQ ID NO: 11)
5'-GGGCCGTCCT AGGATGACCT GAGTACTGTC CGCCCAACGG

TGTGACGGCC CTGCGATCAA-3'

#22
                                             (SEQ ID NO: 12)
5'-CCCTCGCCCT GAGTACTGTC CCCCGTCCGT CCGGTGAGGG

CCACTATCGC TAACTGATCA-3'

#4
                                             (SEQ ID NO: 13)
5'-AGGCCGTTGG TGTGGTGGGC CTAGGGCCGG CGGCGCACAG

CTGTTATAGA CGTCTCCAGC-3'

#12-5
                                             (SEQ ID NO: 14)
5'-CCGCCGTTGG TGTGGTGGGC CTAGGGCCGG CGGCGCACAG

CTGTTATAGA CGTCTCCAGC-3'

#6
                                             (SEQ ID NO: 15)
5'-CCGCCGTTGG TGTGGTGGGC CTAGGGCCGG CGGCGCACAG

CTGTTATAGA CGCCTCCAGC-3'

#12-7
                                             (SEQ ID NO: 16)
5'-CCGCCGTTGG TGTGGTGGGC CCAGGGCCGG CGGCGCACAG

CTGTTATAGA CGCCTCCAGC-3'

#12-2
                                             (SEQ ID NO: 17)
5'-TGACGGTGGC GTGGAGGGCG CGTATCAATC GTTGATCGCA

GGGCCGTCAT ACCGTTGGAG-3'

#12-9
                                             (SEQ ID NO: 18)
5'-TGACGGTGGC GTGGAGGGCG CGTATCAATC GTTGATCGCA

GGGCCGTCAT ACCGTTGGGGG-3'

#12-6
                                             (SEQ ID NO: 19)
5'-TGACGGTGGC GTGGAGGGCG CGTATCAATC GTTGATCGCA

GGGCCGTCAT ACCGGTCGGG-3'

#2
                                             (SEQ ID NO: 20)
5'-GCCGACAGGG CATGGGACGC TATCAGCGGT GTCAATCGAA

TTCCCGCGGC CGCCATGCGG-3'
```

-continued

14
(SEQ ID NO: 21)
5'-GGTCCCCGCA GCTCATACGG CGCTCCAGCG TAATCGAATT

CCCGCGGCCG CCATGCGGCC-3'

46
(SEQ ID NO: 22)
5'-GCGAGTGGCC CATCAGCAGA GCGTAATCCC CACGCACATC

GAGTGCCCCC GGCCGGTGCT-3'

12
(SEQ ID NO: 23)
5'-GTATTGTCAT TCATATCCTC GTGCTTGCTG TCCTCACCCC

ACCCACCAGA ATGGAAA-3'

13
(SEQ ID NO: 24)
5'-CCTGGTATTG TCTTGCCAAT CCTCGCCCTG GCTGTCTTAC

CCCTCCCCAC CCGCCTGAAG-3'

48
(SEQ ID NO: 25)
5'-GTCGACTCGC GGGTACCGTG CTCAATGTCC CAATCCGGGG

AAGCGTTTAG ACCCGCAGCC CAC-3'

40
(SEQ ID NO: 26)
5'-GTCGCCACTG CGGGTACCGT GCTTGGGCNA CCGATGNACC

NTGNNACCGT GTTTNGCC-3'

3
(SEQ ID NO: 27)
5'-CCGGTGGGTG GTCAGGTGGG ATAGCGTTCC GCGTATGGCC

CAGCGCATCA CGGGTTCGCA CCA-3'

32
(SEQ ID NO: 28)
5'-GGGCGGTGGG TGGCGAGTTG TGAGACGCTG GAGGAGGTTG

CTGCCCCCGG CACATTGGGA-3'

1-2: Preparation of Sol-gel Chip

Figure 3:
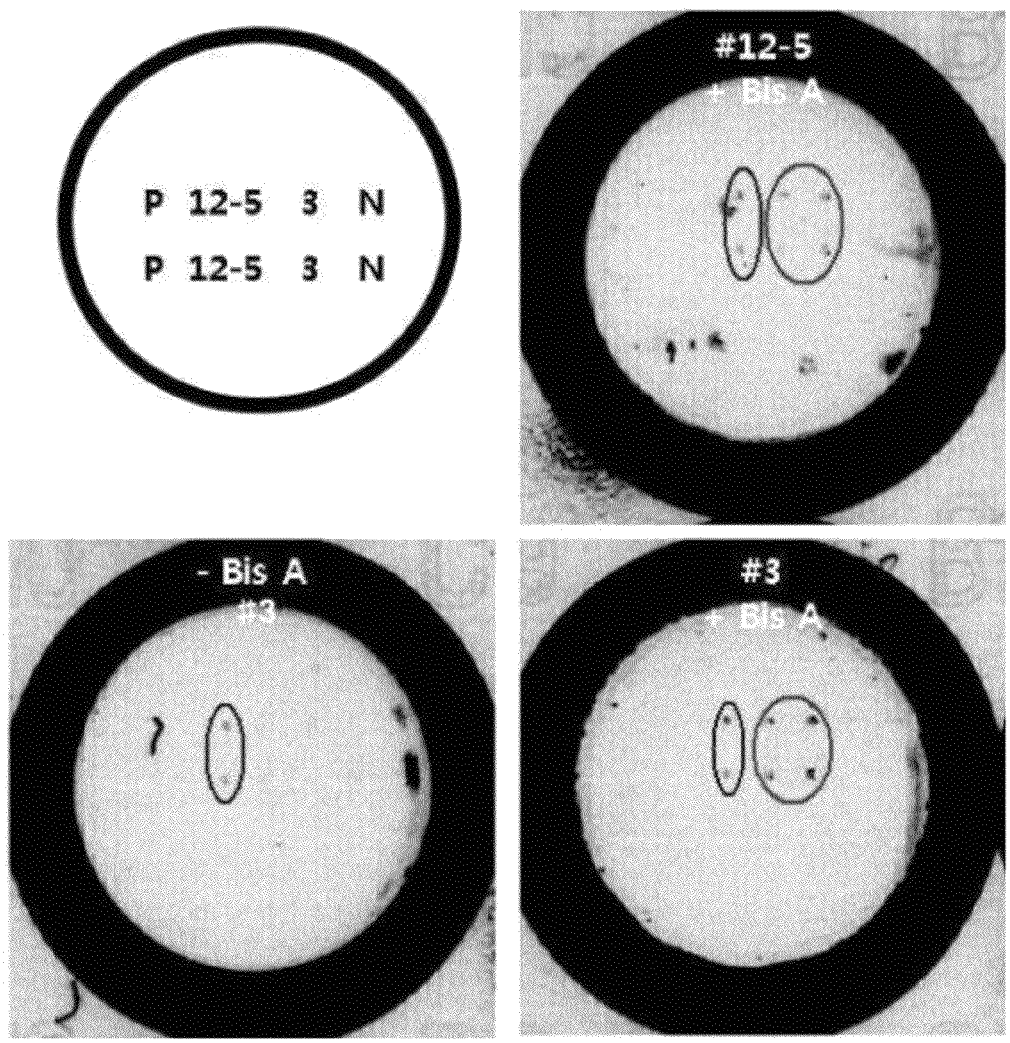
FIG. 3 shows the results of carrying out the detection of bisphenol A by sandwich binding according to the method of the present invention.

A sensor chip having the first aptamer immobilized thereon was prepared in the following manner. As shown in FIG. 3, sol-gel spots together with a negative control, aptamers (#3 and #12-5) and a positive control were immobilized on PMMA-coated 96-well plates in order of the positive control (P), aptamer #12-5, aptamer #3 and the negative control (N) using OmniGrid Accent Microarrayer (DIGI LAB, USA), thereby preparing sol-gel chips.

A composition for forming the so-gel spots was prepared in the following manner. First, tetramethyl orthosilicate (TMOS) and methyltrimethoxysilicate (MTMS) were mixed with each other to prepare a sol composition. Also, 100 mM HCl was prepared as solution I.

Meanwhile, 100 mM SP buffer (pH 5.8) and 20 μl of double distilled water (DDW) were mixed with each other, after which 10 μl of each of Cy3 antibody (Santa Cruz, USA) for the positive control, PBS buffer for the negative control, and the selected aptamers (#3 and #12-5) was added to the mixture and vortexed for 5 seconds and spun-down, thereby preparing solution II.

Next, the sol composition, the solution I and the solution II were sequentially dispensed, and the resulting sol-gel spots were gelled for 13-15 hours, thereby preparing sol-gel chips.

Example 2

Detection of Bisphenol A Using Sol-gel Chip

First, aptamers #3 and #12-5 were labeled with terminal deoxynucleotidyl transferase (Fermentas, Canada) and Cy3-dUTP (GeneChem, Korea) and used in this Example. However, labeling may also be performed by linking a fragment such as 5'-GGGCCGTTCGAACACGAGCATG-3' (SEQ ID NO: 29) to the end of each of aptamers #3 and #12-5 (serving as the second aptamers), attaching Cy3 to a nucleic acid fragment such as 5'-CATGCTCGTGTTCGAACGGCCC-3' (SEQ ID NO: 30) capable of complementarily binding to the fragment linked to the second aptamer, and complementarily binding the Cy3-labeled nucleic acid fragment to the fragment linked to the end of the second aptamer.

Then, 50 μM of bisphenol A and 2 μM of the Cy3-labeled aptamer (second aptamer) were added to each well of the sol-gel chips prepared in Example 1-2. Specifically, as shown in FIG. 3, the upper right well was treated with bisphenol A (BPA) and aptamer #12-5, the lower left well with buffer and aptamer #3, and the lower right well with BPA and aptamer #3, and the wells were incubated. Next, the wells were washed and then analyzed by a Multi-Image analyzer (FUJIFILM, Japan).

As a result, as shown in FIG. 3, signals (indicated by red circles) appeared at the positions of immobilized aptamers #12-5 and #3 only when bisphenol A was present, suggesting that the use of the sol-gel chip according to the present invention can specifically detect bisphenol A. Specifically, even non-polar, low-molecular-weight bisphenol A which was difficult to detect by prior art methods was specifically detected by the method of the present invention.

Example 3

Fabrication of FET-CNT Sensor for Detecting Bisphenol A

Using the aptamer isolated in Example 1, a single-walled carbon nanotube (swCNT)-FET sensor chip according to a method (Lee, M. et al., *Nat. Nanotechnol.*, 1:66, 2006) known in the prior art. A methyl-terminated octadecyltrichlorosilane (OTS) self-assembled monolayer was patterned on a SiO₂ substrate by conventional photolithography to create non-polar, passivating molecular patterns. For this purpose, the substrate was dipped in a solution of 0.05 mg/ml of single-walled carbon nanotubes (swCNTs) in o-dichlorobenzene, and swCNTs were assembled directly at $SiO_2$ sites and aligned. Electrodes were patterned on the substrate by photolithography, and Pd and Au (30 nm Au on 10 nm Pd) were thermally deposited on the substrate according to a lift-off process.

In order to provide a swCNT-based sensor for detection of bisphenol A, aptamer #3 (SEQ ID NO: 3) among the above-obtained 27 aptamers binding specifically to bisphenol A was immobilized on the Au electrode of the swCNT-FET sensor chip. For immobilization, the chip was pretreated with MCH by dipping it in 10 nM MCH (mercaptohexanol) solution (in neutralized water) overnight. Then, the chip was dipped in 1 μM aptamer in buffer (10 nM Tris-HCl) for 10 hours, whereby the gold electrode was coated with the ssDNA aptamer having a thiol group at the 5' end and binding specifically to bisphenol A, thereby fabricating an FET sensor for detection of bisphenol A.

Example 4

Detection of Bisphenol A Using FET-CNT Sensor

Electrical detection of bisphenol A (BPA) was performed by monitoring changes in electric current (source-drain bias: 0.1V), induced by introduction of BPA or other molecules, using Keithley 4200 semiconductor analyzer (USA).

Figure 4:
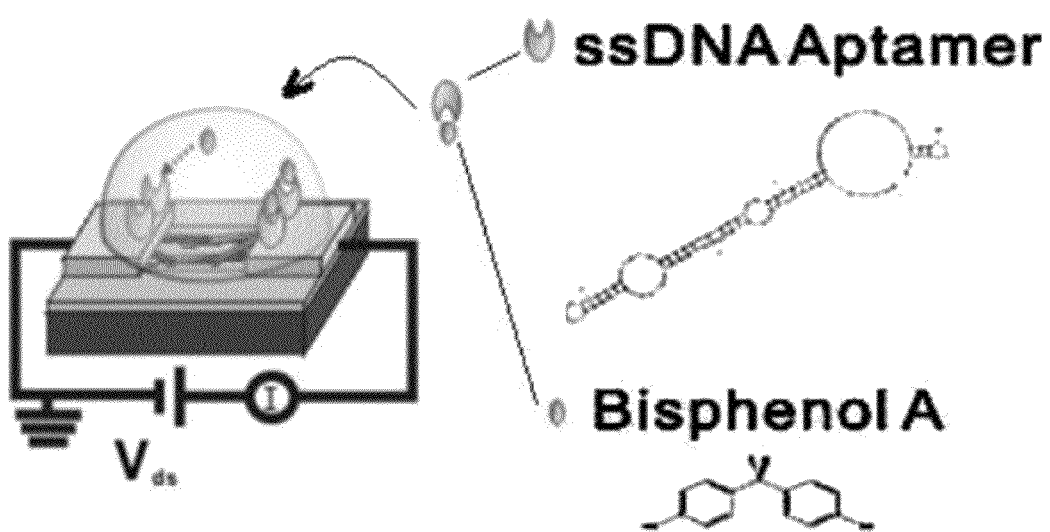
FIG. 4 is a schematic view showing a process of detecting bisphenol A (BPA) using a swCNT-FET sensor and the method of the present invention.

First, for a control group, while the source-drain current change was monitored, various concentrations (1 pM to 100 nM) of a BPA solution in a binding buffer (100 mM Tris-HCl, 200 mM NaCl, 25 mM KCl, 10 mM $MgCl_2$, 2.5 ppm DMSO) were added to the sensor fabricated in Example 3. For a test group, BPA having bound thereto aptamer #3 (SEQ ID NO: 5; second aptamer) binding specifically to bisphenol A was added at various concentrations (1 pM to 100 nM) to the sensor fabricated in Example 3 (see FIG. 4). Herein, the BPA having aptamer #3 (second aptamer) bound thereto was prepared in the following manner. First, BPA and the aptamer solution were mixed with each other at the same concentration, after which the mixed solution was heated at 95° C. for 5 minutes and cooled to room temperature over 1-2 hours. In addition, for a control group, an aptamer solution containing aptamer #3 alone without BPA was added to the sensor, fabricated in Example 3, under the same conditions as described above.

Meanwhile, in order to examine whether the fabricated FET sensor for detection of BPA specifically detects only BPA, each of bisphenol B (BPB), 4,4'-bisphenol (BP) and 6F bisphenol A (6F), which have structures similar to that of BPA, was introduced at a concentration of 1 nM.

Figure 5:
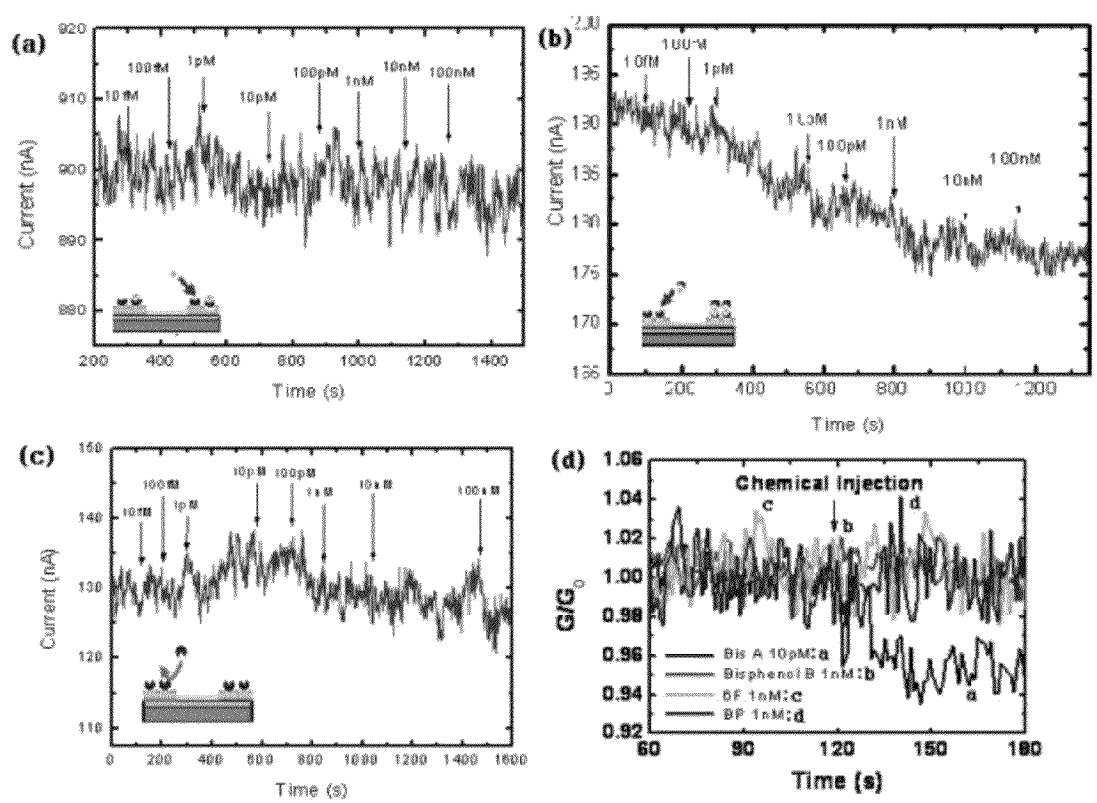
FIG. 5 is a set of graphs showing the results of measuring changes in electric current, occurred when each of a BPA solution (a), a mixed solution of BPA and anti-BPA aptamer (b) and an anti-BPA aptamer solution (c) was added to a swCNT-FET sensor and when a mixed solution of an anti-BPA aptamer solution and each of BPA, BPB, 6F and BP solutions (d) was added to a swCNT-FET sensor.

As a result, as shown in FIG. 5a, in the case in which the bisphenol A solution alone was added, the FET sensor chip did not detect the non-polar molecule bisphenol A even when bisphenol A was added at a concentration of 100 nM. This is because BPA itself does not have any charge or dipole. On the other hand, when the bisphenol A-containing sample was added together with the second aptamer by the method of the present invention, the signal was clearly different from the background signal as shown in FIG. 5b, suggesting that the non-polar molecule bisphenol A can be detected from a concentration of 1 pM according to the method of the present invention. Also, as shown in FIG. 5c, when the second aptamer alone was added to the sensor without bisphenol A, no significant change did occurred, like FIG. 5a.

Also, as shown in FIG. 5d, bisphenol B (BPB), 4,4'-bisphenol (BP) and 6F bisphenol A (6F), which have structures similar to that of bisphenol A (BPA), were introduced, no significant change in electric current occurred.

The above experimental results suggest that the detection method according to the present invention can specifically detect even a non-polar, low-molecular-weight mole in a solution, which could not be detected by conventional FET sensors due to transfer of excessively low charges.

Example 5

Multi-channel AAO (Anodic Aluminum Oxide) Sensor-based Detection of Target Material Using Aptamer 5-1: Fabrication of AAO Sensor The AAO (anodic aluminum oxide) sensor used in this Example was fabricated in the following manner.

(1) A metal pattern formed of 1.3 μm thick aluminum, 5 nm thick gold and 10 nm thick titanium, deposited using an electron beam evaporator, was formed on a silicon substrate having a 200 nm thick silicon dioxide layer, by photolithography using a lift-off process.

(2) Nano-sized pores of anodic aluminum oxide had a diameter of about 75 nm and were formed by a two-step anodic oxidation process (Masuda, H., Fukuda, K., 1995. Science 268 (5216), 1466-1468). The aluminum film deposited in the first step of anodic oxidation was anodized in 0.3M oxalic acid at room temperature at a constant voltage of 40V for 5 minutes. The anodic aluminum oxide film was then dissolved in a 1.8 wt % chromic acid solution at 70° C., and then anodized for 5 minutes. The boundary layer of the anodic aluminum oxide was removed by dipping it in a 6 wt % phosphoric acid solution at room temperature, and 450 nm thick silicon dioxide was deposited on the outer side of the anodic aluminum oxide region.

(3) A gold nanowire serving as a bottom electrode at a constant voltage of 1.1 V in an electrolyte solution of hydrogen tetrachloroaurate ($HAuCl_4$; adjusted to a pH of 4 by addition of sulfuric acid). The top gold electrodes (0.3×5.5 mm) were made on the anodic aluminum oxide region by photolithography using a lift-off process.

(4) Then, PDMA microfluidic channels were mounted on the sensor array.

5-2: Detection of Target Material Using AAO Sensor

The AAO sensor fabricated in Example 5-1 was connected to a flow system, 10 nM of an aptamer (aptamer #3 of SEQ ID NO: 27) having a thiol group attached to the 3' end thereof was dissolved in a binding buffer (25 mM Tris-HCl, 100 mM NaCl, 25 mM KCl, 10 mM $MgCl_2$, pH 8.0) and then incubated overnight while it was introduced into the AAO sensor at a rate of 0.1 ml/hr. Because the surface of the AAO sensor was coated with gold particles, the thiol group at the 3' end of the aptamer was covalently bonded with the gold particles, whereby the aptamer was bound to the surface of the AAO sensor. For a control group, a sensor in which a binding buffer alone was introduced without the aptamer and incubated was used. A bisphenol A binding buffer was introduced at a rate of 0.5 ml/hr for 1 hour and prepared as a reference buffer level. Bisphenol A was introduced at concentrations of 1 nM, 10 nM and 100 nM into the sensor, which was then washed with a binding buffer, after which the capacitance (nF) of the sensor was measured. In order to determine a frequency at which capacitance is to be measured, a frequency sweep experiment was carried out.

Figure 7:
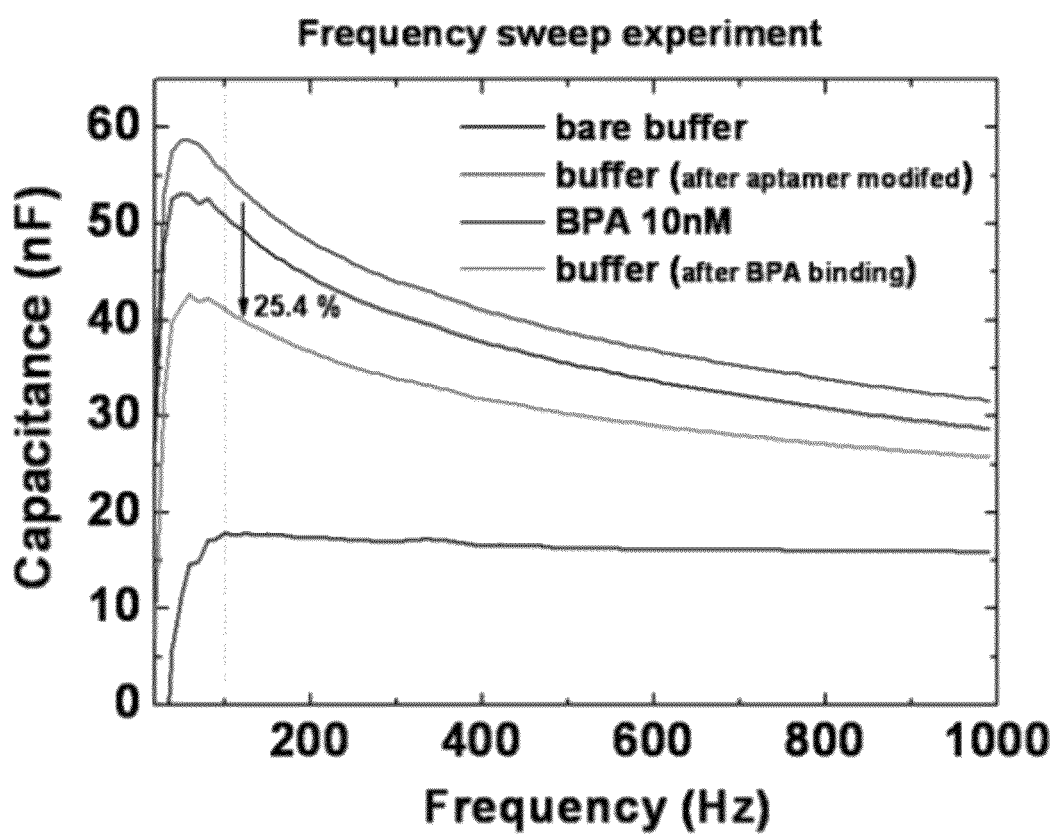
FIG. 7 shows the results of measuring capacitance in the frequency range from 0 to 1000 Hz when an aptamer was bound to a sensor and when bisphenol A was introduced into a sensor.

While frequency was changed from 0 Hz to 1000 Hz, capacitance was measured when the aptamer was bound to the sensor and when bisphenol A was introduced into the sensor. As a result, as shown in FIG. 7, the most ideal results were shown at 100 Hz. Thus, in subsequent experiments, capacitance was measured at 100 Hz.

Meanwhile, for a control group, an AAO sensor to which no aptamer was bound was used, and for an experimental group, an AAO sensor to which the aptamer was bound was used to carry out an experiment on the detection of bisphenol A.

Figure 8:
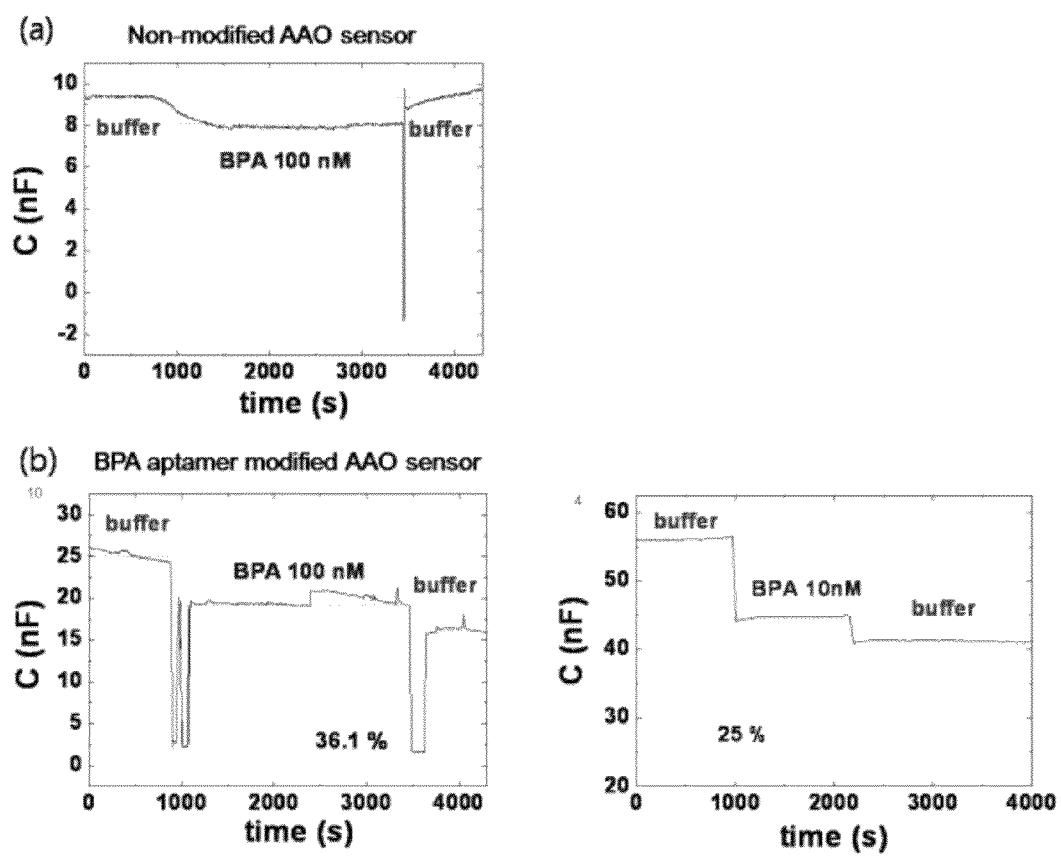

As a result, as shown in FIG. 8a, in the AAO sensor to which no aptamer was bound, there was no change in capacitance when bisphenol A introduced into the AAO sensor. However, as shown in FIG. 8b, in the AAO sensor to which the aptamer was bound, capacitance decreased by 25% when 10 nM of bisphenol A was introduced, and it decreased by 36.1% when 100 nM of bisphenol A was introduced.

Figure 9:
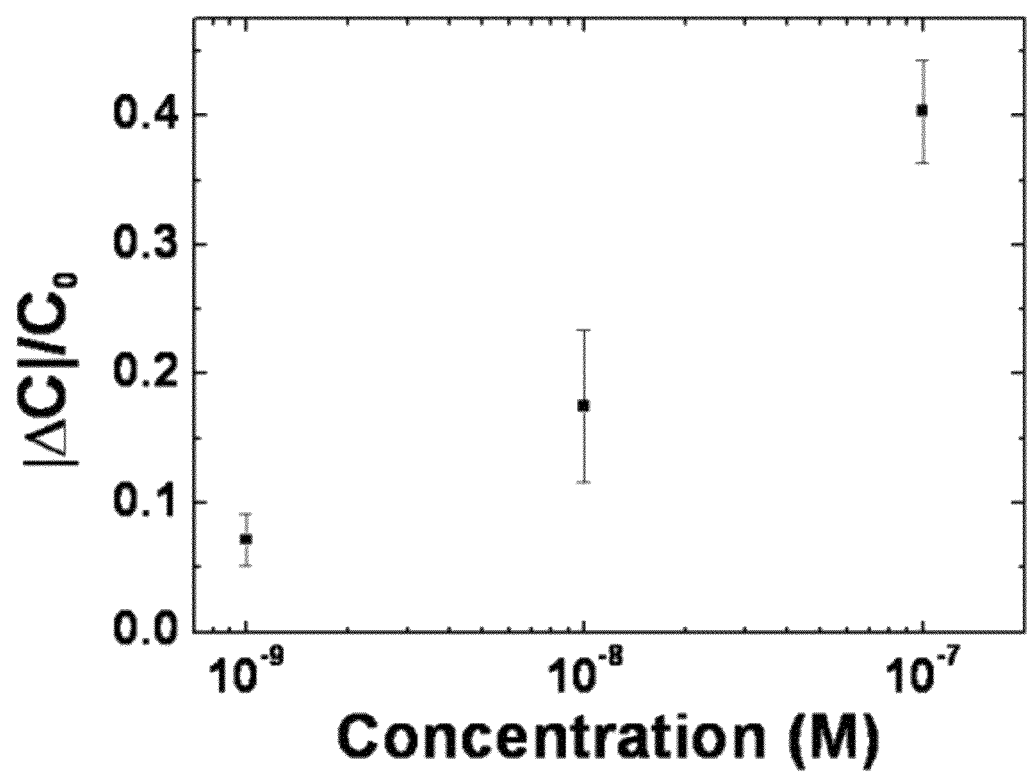
FIG. 9 is a graph showing changes in capacitance when bisphenol A was introduced at concentrations of 1 nM, 10 nM and 100 nM into an AAO sensor to which an aptamer was bound.

In addition, changes in capacitance when bisphenol A was introduced at concentrations of 1 nM, 10 nM and 100 nM are graphically shown in FIG. 9. As can be seen therein, a generally linear graph was drawn, even though there was a slight error at a concentration of 1 nM or less.

The above experimental results suggest that the AAO sensor-based detection method of the present invention can specifically detect even a non-polar, low-molecule-weight molecule in a solution, which could not be detected using prior art methods due to transfer of excessively low charges.

INDUSTRIAL APPLICABILITY

As described above, the inventive method and kit for a target material using an aptamer can detect even low-molecular-weight materials which were difficult to detect in the prior art, thereby enabling detection of disease-related metabolites, environmental pollutants and food toxins in solutions. In addition, the detection method of the present invention is a direct and simple method and is highly cost-effective, because it uses the aptamer which can be consistently reproduced and can be produced at low costs. Thus, the present invention is very useful.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of detecting a small, apolar molecule using aptamers, the method comprising the steps of:
   (a) adding a sample containing a small, apolar molecule, and a second aptamer binding specifically to the small, apolar molecule and having a label attached thereto, to a first aptamer immobilized on a solid phase and binding specifically to the small, apolar molecule, to form a mixture, and incubating the mixture; and
   (b) analyzing the label to detect the small, apolar molecule.

2. The method of claim 1, wherein the label includes fluorescent materials.

3. The method of claim 2, wherein analysis of the fluorescent materials is performed by measuring the generated luminescence or color change of the fluorescent materials.

4. The method of claim 1, wherein the sample is collected from one or more of water, blood, urine, tears, sweat, salvia, lymph, cerebrospinal fluids, soil, air, food, waste, animal and plant organs, and animal and plant tissues.

5. The method of claim 1, wherein the first aptamer or the second aptamer is selected from aptamers represented by nucleic acid sequences of SEQ ID NOS: 2 to 28.

6. The method of claim 1, wherein the small, apolar molecule is bisphenol A.

7. A method of detecting a small, apolar molecule using aptamers, the method comprising the steps of:
   (a) adding a sample containing a small, apolar molecule, and a second aptamer binding specifically to the small, apolar molecule, to a first aptamer immobilized on a solid phase and binding specifically to the small, apolar molecule, to form a mixture, and incubating the mixture;
   (b) binding a label to the second aptamer; and
   (c) analyzing the label to detect the small, apolar molecule.

8. The method of claim 7, wherein binding the label in step (b) is performed by complementarily binding a nucleic acid fragment to the second aptamer, in which the nucleic acid fragment has a label attached thereto and is capable of complementary binding to the second aptamer.

9. The method of claim 8, wherein the nucleic acid fragment complementary bind to one end of the second aptamer.

10. The method of claim 7, wherein the first aptamer or the second aptamer is selected from aptamers represented by nucleic acid sequences of SEQ ID NOS: 2 to 28.

11. The method of claim 7, wherein the small, apolar molecule is bisphenol A.

12. A kit for detecting a small, apolar molecule, the kit comprising: a solid phase having immobilized thereon a first aptamer binding specifically to the small, apolar molecule; and a detection reagent containing a second aptamer binding specifically to the small, apolar molecule.

13. The kit of claim 12, wherein the second aptamer has a label attached thereto.

14. The kit of claim 12, wherein the kit further comprises a nucleic acid fragment having a label attached thereto and being capable of complementary binding to the second aptamer.

15. A kit for detecting bisphenol A, the kit comprising: a solid phase having immobilized thereon a first aptamer binding specifically to bisphenol A; and a detection reagent containing a second aptamer binding specifically to bisphenol A, wherein the first aptamer or the second aptamer is selected from aptamers represented by nucleic acid sequences of SEQ ID NOS: 2 to 28.

16. The method of claim 1, wherein the label is a nucleic acid fragment and being capable of complementarily binding to the end of the aptamer.

\* \* \* \* \*